(12) United States Patent
Deng et al.

(10) Patent No.: US 9,416,423 B2
(45) Date of Patent: Aug. 16, 2016

(54) PRIMER GROUP FOR DETECTING CPG ISLAND METHYLATION OF P16 GENE USING METHYLATION-SPECIFIC FLUORESCENCE TECHNIQUE

(75) Inventors: Dajun Deng, Beijing (CN); Jing Zhou, Beijing (CN)

(73) Assignee: Beijing Institute For Cancer Research (CN)

( * ) Notice: Subject to any disclaimer, the term of this patent is extended or adjusted under 35 U.S.C. 154(b) by 412 days.

(21) Appl. No.: 13/978,956

(22) PCT Filed: Jan. 1, 2011

(86) PCT No.: PCT/CN2011/000048
§ 371 (c)(1),
(2), (4) Date: Apr. 15, 2015

(87) PCT Pub. No.: WO2012/094776
PCT Pub. Date: Jul. 19, 2012

(65) Prior Publication Data
US 2015/0218642 A1    Aug. 6, 2015

(51) Int. Cl.
*C12Q 1/68* (2006.01)
(52) U.S. Cl.
CPC ............ *C12Q 1/6886* (2013.01); *C12Q 1/6883* (2013.01); *C12Q 2600/154* (2013.01)
(58) Field of Classification Search
None
See application file for complete search history.

(56) References Cited

U.S. PATENT DOCUMENTS

2005/0227265 A1* 10/2005 Barany et al. ............... 435/6
2006/0252043 A1* 11/2006 Bai et al. ..................... 435/6
2008/0286761 A1* 11/2008 Day et al. .................... 435/6

FOREIGN PATENT DOCUMENTS

WO    WO 2007009755 A2 *  1/2007

OTHER PUBLICATIONS

Cao et al. (Methylation of p16 CpG Island Associated with Malignant Progression of Oral Epithelial Dysplasia: A Prospective Cohort Study, Clin Cancer Res. Aug. 15, 2009;15(16):5178-83. Epub Aug. 11, 2009).*
Campan et al. (MethyLight, CH 23, in DNA Methylation: Methods and Protocols, Second Edition, vol. 507, Humana Press, Jorg Tost (ed.), Nov. 28, 2008).*
Premier Biosoft (attached, available at http://www.premierbiosoft.com/molecular_beacons/index/methylight.html, May 28, 2001).*
Buck et al. ("Design Strategies and Performance of Custom DNA Sequencing Primers," Biotechniques. 1999. 27(3): pp. 528-536).*
Lowe et al. (Nucleic Acids Research, vol. 18, No. 7, p. 1757-1761, 1990).*

* cited by examiner

*Primary Examiner* — Aaron Priest
(74) *Attorney, Agent, or Firm* — Schwegman Lundberg & Woessner, P.A.

(57) ABSTRACT

The invention provides a primer group for detecting CpG island methylation of p16 gene using methylation specific fluorescence technique. The primer group comprises a pair of oligonucleotide primers and a fluorescence-labeled probe. Said oligonucleotide primer pair has base sequence represented by SEQ ID NO.1 and SEQ ID NO.2. Said fluorescence-labeled probe has base sequence represented by SEQ ID NO.3 or SEQ NO.4.

3 Claims, 1 Drawing Sheet

SEQUENCE LISTING

```
<160> NUMBER OF SEQ ID NOS: 13

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
cgcggtcgtg gttagttagt                                              20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
tacgctcgac gactacgaaa                                              20

<210> SEQ ID NO 3
<211> LENGTH: 20
<212> TYPE: DNA
<213> ORGANISM: Artificial Sequence
<220> FEATURE:
<223> OTHER INFORMATION: probe

<400> SEQUENCE: 3 gttgttttc gtcgtcggtt                                               20

<210> SEQ ID NO 4
<211> LENGTH: 20
<212> TYPE: DNA
<213> ORGANISM: Artificial Sequence
<220> FEATURE:
<223> OTHER INFORMATION: probe

<400> SEQUENCE: 4 gttgttttc gtcgttcgtt                                               20

<210> SEQ ID NO 5
<211> LENGTH: 28
<212> TYPE: DNA
<213> ORGANISM: Artificial Sequence
<220> FEATURE:
<223> OTHER INFORMATION: primer

<400> SEQUENCE: 5
tctaacaatt ataaactcca accaccaa                                     28
```

```
<210> SEQ ID NO 6
<211> LENGTH: 25
<212> TYPE: DNA
<213> ORGANISM: Artificial Sequence
<220> FEATURE:
<223> OTHER INFORMATION: primer

<400> SEQUENCE: 6
gggaagatgg gatagaaggg aatat                                          25

<210> SEQ ID NO 7
<211> LENGTH: 36
<212> TYPE: DNA
<213> ORGANISM: Artificial Sequence
<220> FEATURE:
<223> OTHER INFORMATION: probe

<400> SEQUENCE: 7
ccttcattct aacccaatac ctatcccacc tctaaa                              36

<210> SEQ ID NO 8
<211> LENGTH: 359
<212> TYPE: DNA
<213> ORGANISM: Artificial Sequence
<220> FEATURE:
<223> OTHER INFORMATION: modified sense chain of p16M gene CpG island

<400> SEQUENCE: 8
tttttttttt tttcggagaa tcgaagcgtt atttgatttt aattttttg taaatttcgt     60 ttttttagagt cgttcgttat tttttgtttt cgttgtagat tttttattta tttggatcgg   120
ttttcgatcg taattattcg gtgcgttggg tagcgttttc gttttagta gcgttcgtat     180 tttttttatt cgatttcggg tcgcggtcgt ggttagttag ttagtcgaag gttttatgtt    240 gttttcgtc gtcggtttta tgttgttttt cgtcgttcgt tgtttgtttt ttttttttc      300 gtagtcgtcg agcgtacgcg gttcgtttta tttttggtg attagttagt ttttttttt      359

<210> SEQ ID NO 9
<211> LENGTH: 24
<212> TYPE: DNA
<213> ORGANISM: Artificial Sequence
<220> FEATURE:
<223> OTHER INFORMATION: primer

<400> SEQUENCE: 9
ttattagagg gtggggcgga tcgc                                           24

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
gaccccgaac cgcgaccgta a                                              21

<210> SEQ ID NO 11
<211> LENGTH: 22
<212> TYPE: DNA
<213> ORGANISM: Artificial Sequence
<220> FEATURE:
<223> OTHER INFORMATION: primer
```

```
<400> SEQUENCE: 11
tggagttttc ggttgattgg tt                                                22

<210> SEQ ID NO 12
<211> LENGTH: 19
<212> TYPE: DNA
<213> ORGANISM: Artificial Sequence
<220> FEATURE:
<223> OTHER INFORMATION: primer

<400> SEQUENCE: 12
aacaacgccc gcacctcct                                                    19

<210> SEQ ID NO 13
<211> LENGTH: 18
<212> TYPE: DNA
<213> ORGANISM: Artificial Sequence
<220> FEATURE:
<223> OTHER INFORMATION: probe

<400> SEQUENCE: 13
acccgacccc gaaccgcg                                                     18
```

PRIMER GROUP FOR DETECTING CPG ISLAND METHYLATION OF P16 GENE USING METHYLATION-SPECIFIC FLUORESCENCE TECHNIQUE

RELATED APPLICATIONS

This application is a nationalization under 35 U.S.C. §371 from International Application Serial No. PCT/CN2011/000048, filed Jan. 11, 2011 and published as WO 2012/094776A1 on Jul. 19, 2012, the contents of which application and publication are incorporated herein by reference in their entirety.

A primer set in the methylation-specific fluorescence assay used to detect methylation of CpG islands in the p16 gene

TECHNICAL FIELD

The present invention relates to PCR primer set used in genetic engineering, specifically, relates to the primer set in the methylation-specific fluorescence assay used to detect methylation of CpG islands in the p16 gene.

BACKGROUND ART

Aberrant methylation of CpG islands in the p16 (CDKN2A) gene can be used for early prediction of malignant transformation of epithelial dysplasia, a precancerous lesion (Sun et al. Clin Cancer Res 2004, 10:5087-5093; Cao et al. Clin Cancer Res 2009, 15:5178-5183). The related artificial nucleotide sequences used in these studies and their uses were granted the patent rights in China and in Europe (Chinese Patent No. ZL03826140.5: European Patent No. EP1602631).

In these studies, the methylation is detected using the method including following steps: sodium bisulfite modification of unmethylated cytosines in the CpG island; after the sodium bisulfite modification, the sequence of sense-strand DNA is no longer complementary to the antisense-strand DNA, and the double-stranded DNA becomes 2 single-stranded DNAs. The sodium bisulfite-modified single-strand antisense DNA is a good template for designing amplification primers used in a methylation-specific PCR assay (150 bp p16-MSP; Herman et al PNAS 1996, 93:9821-9826) and quantitative methylation-specific 70 bp fluorescence assays (MethyLight; Ead et al. Cancer Res 2000, 60:5021-5026), which are commonly used in scientific researches.

In our prospective epidemiological follow-up cohort study, we have found that methylated p16 (p16M) detected with the 150 bp-MSP method (150 bp p16-MSP; Herman et al PNAS 1996, 93:9821-9826) can be used to predict malignant transformation of oral mucosal epithelium. The sensitivity and specificity of prediction in the elderly over 60 years old are 76.9% and 78.3%, respectively (Cao et al, Clin Cancer Res 2009, 15:5178-5183). These results show that these CpG sites in the p16 genes may have important application value.

As a qualitative assay, the 150 bp-MSP assay can't meet with the requirements for developing diagnostic kit, because said diagnostic kit need to use the sequence-specific probes as to confirm and make the quantitative determination. If the results of 150 bp-MSP analysis are used as the gold standard, we have found that the qualitative results (without setting of a cut-off value) of the 70 bp-MethyLight fluorescence analysis (MethyLight; Ead et al. Cancer Res 2000, 60:5021-5026) has a higher sensitivity (37/44=84.1%), poor specificity (20/58=34.5%), and low accuracy (84.1%+34.5%−1=18.6%), as shown in FIG. 1. Even though the employment of a cut-off value in the MethyLight analysis can improve its accuracy, statistically significant correlation still cannot be observed between the MethyLight determination and clinical outcomes. Apparently, the 70 bp-MethyLight fluorescence method can not meet the requirements of the development of diagnostic kits.

DISCLOSURE OF THE INVENTION

The objective of the present invention is to provide a primer set in the methylation-specific fluorescence assay used to detect methylation of CpG islands in the p16 gene, having high sensitivity, specificity, and accuracy when using said primer set to detect methylation of CpG islands in the p16 gene. Therefore, this primer set is expected to meet the requirements of the development of diagnostic kit.

To this end, the present invention provides a primer set in the methylation-specific fluorescence assay used to detect methylation of CpG islands in the p16 gene, comprising a pair of oligonucleotide primers and one fluorescence-labeled probe, characterized in that said a pair of oligonucleotide primers have the base sequence as shown in SEQ ID NO.1 and SEQ NO.2, and said fluorescence-labeled probe has base sequence as shown in SEQ ID NO. 3 or SEQ ID NO.4.

Another characteristic of this primer set in the present invention is that said primer set is designed based on the nucleotide sequences of the sense-strand or its complementary antisense-strand of the methylated CpG islands of p16 gene after sodium bisulfite modification. Further, said nucleotide sequence of the sense-strand has the base sequence as shown in SEQ ID NO.8.

Comparative studies have shown that, if the result of MSP analysis is used as the gold standard and no cut-off value is used, the novel method using this primer set in the present invention has high sensitivity (26/44=59.1%) and high specificity (56/58=98.3%), with 57.4% accuracy that is 3 times for the classic 70 bp-MethyLight assay (FIG. 1). When a cut-off value is used in the novel MethyLight assay, the similar results are still observed. Most importantly, results of the novel assays show that the risk of malignant transformation of oral epithelial dysplasia lesions containing the methylated CpG islands of p16 gene in the patients in the above mentioned follow-up study is significantly higher than that not containing the methylated CpG islands of p16 gene (6/8 vs. 6/22; P=0.036, two-sided). This is a case of use of the methylated CpG islands of p16 gene disclosed by the prior art (China Patent No. ZL03826140.5; European Patent No. EP1602631), which indicates that the primer set has the industrial application.

BRIEF DESCRIPTION OF ATTACHED DRAWINGS

THE BEST EMBODIMENTS TO CARRY OUT THE PRESENT INVENTION

Example

Figure 1:
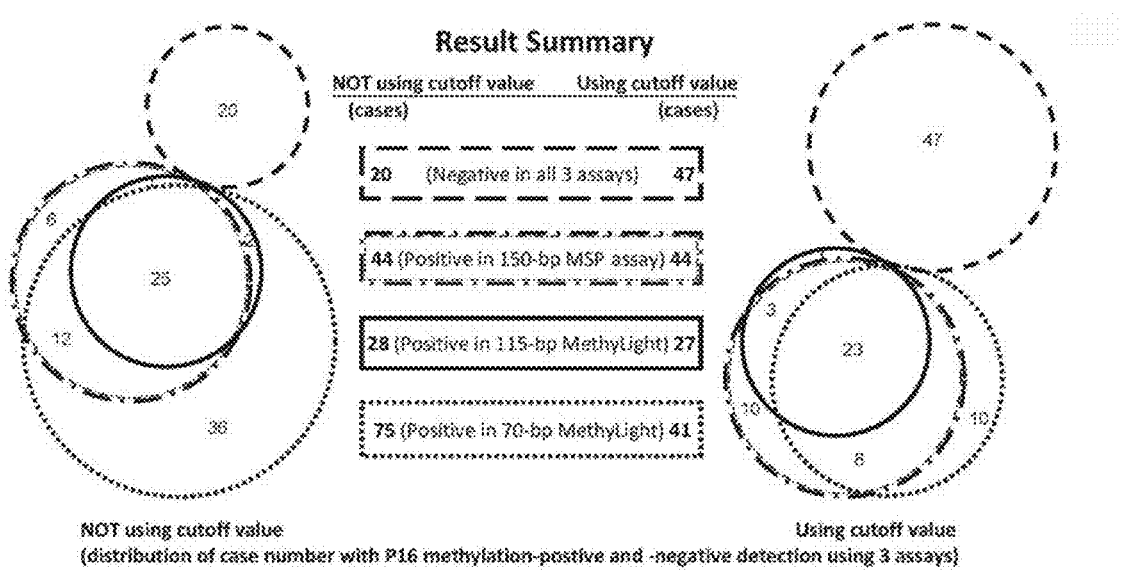
FIG. 1 is the summary of results using different methods to determine the methylated p16 CpG islands in 102 human epithelial dysplasia tissue samples. The right and left charts respectively illustrate the results when the cut-off value is used, and not used in two MethyLight fluorescence assays.

1. Regularly digest tissue protein using proteinase K; extract genetic DNA samples from 102 human epithelial dysplasia tissue samples using ethanol precipitation method.

2. Convert the unmethylated cytosine in the DNA samples using 5M sodium bisulfite, including following steps.
   1) Add and dissolve 2 µg DNA sample into a tube with 18 µl sterile distilled water; incubate in the water bath at 95° C. for 20 min, and then incubate in the ice bath.
   2) Add 2 µl of 3M NaOH solution into the DNA-containing tube, mix, and incubate in the water bath at 42° C. for 20 min to denature the DNA.
   3) Preparation of fresh solution of 5.0M NaHSO$_3$ (4 ml): subsequently add 1.9 g Na$_2$S$_2$O$_5$, 0.7 ml of 2M NaOH, and 0.5 ml of 1M hydroquinone into 2.5 ml of sterile triple-distilled water; incubate in a water bath at 50° C., with repeatedly inverting and mixing until completely dissolved;
   4) Add 380 µl of 5.0M NaHSO$_3$ into the DNA-containing tube, mix well, then add the 200 µl of liquid paraffin onto the top surface of the solution in the tube to prevent the evaporation of the liquid in the tube. Incubate the paraffin sealed tube in a water bath at 50° C. overnight to convert the unmethylated cytosine to uracil;
   5) Remove the liquid paraffin solution; purify the modified DNA using DNA purification kit (Promega Wizard DNA Clean-Up System, A7280) according to the instructions: add 1 ml of the mixture of resin, then stay for 5 minutes after mixing; transfer the resin-DNA mixture into an injector tube connected to a micro-column filter; remove liquid phase and transfer the DNA sample onto solid phase in the micro-column filter through vacuum; add 2 ml of 80% isopropyl alcohol, remove the liquid within the injector-filter through vacuum, and disconnect the injector tube; set the micro-column filter into another centrifuge tube (1.5 ml), centrifuge at high-speed (10,000 g, 20 seconds) to remove residual liquid in the column filter; set the micro-column filter to another centrifuge tube, add 40 µl of TE buffer (at 80° C.) into the micro-column, stand for 10 min, centrifuge at high-speed (10,000 g, 20 seconds) to collect the eluent, and store at −20° C.;
3. Synthesize the oligonucleotide primers having SEQ ID NO.1 and SEQ ID NO.2 for the methylated CpG islands of p16 gene. Synthesize fluorescence-labelled TagMan probe having SEQ ID NO. 3 or SEQ ID NO.4;
4. Add 1 µl template into 20 µl PCR reaction mixture; amplify the methylated p16 CpG islands in the tested DNA samples using the oligonucleotide primers and TagMan probe; read the Ct value in a real-time quantitative PCR instrument;
   Preparation of PCR reaction mixture: 100 µl mixture including
      10 µl 10×PCR buffer (Qiagen),
      2.5 U HotStar Taq enzyme (Qiagen),
      200 µM dATP, dCTP, dGTP (Promage),
      800 µM dUTP (Promage),
      5 mM MgCl$_2$,
      75 nM Primer (the TaKaRa synthetic),
      75 nm Probe (the TaKaRa synthetic),
      2 U UNG enzyme (NEB),
      10 µl 10×UNG enzyme buffer (NEB)
   PCR thermal cycle conditions: 37° C. for 10 min→95° C. for 30 min→45 cycles (95° C. for 15 sec→62° C. for 1 min); detect the Ct fluorescence value at 62° C.; the Quantitative PCR instrument: ABI7500
5. In the same time, the corresponding sequence of the COL2A gene (but not limited to the gene), not containing CpG site, is used as a reference gene to represent the amount of the bisulfite-modified DNA templates in the tested samples as reported in the literature (Widschwendter et al. Cancer Res 2004, 64:3807-3813). The amount of the COL2A gene is amplified with the corresponding oligonucleotide primers (SEQ ID NO.5 and SEQ ID NO.6) and the fluorescence-labeled probe (SEQ ID NO.7; 6FAM-Col2a$^{probe}$-BHQ1 TaqMan). The Ct value is read by the quantitative PCR instrument;
6. Calculate the content (relative copy number) of p16M in the tested sample using the formula $[2^{-(Ct_{p16M}-Ct_{COL2a})}]$, based on both Ct values;
7. In the same time, amplify the methylated p16 gene in the above samples using the primers SEQ ID NO 9 and SEQ ID NO.10 in the 150 bp-MSP assay (150 bp, p16-MSP; Herman et al PNAS 1996, 93:9821-9826);
8. In the same time, amplify the methylated p16 gene in the above samples using the primers SEQ ID NO 11 and SEQ ID NO.12 and specific probe SEQ ID NO.13 in the quantitative methylation-specific fluorescence assay (70 bp MethyLight, Ead et al, Cancer Res 2000, 60: 5021-5026).

Final Results:

Of the 102 tested human epithelial dysplasia tissue samples, 44 samples are p16M-positive and 58 samples are p16M-negative in the 150 bp-MSP assay; 75 samples are p16M-positive in the 70 bp fluorescence MethyLight assay; 28 samples are p16M-positive in the 115 bp novel MethyLight assay (method of the invention). p16M are not detectable in 20 samples in any of these three assays.

The results of 150 bp-MSP assay is of potential of clinical application (Cao et al. Clin Cancer Res 2009, 15:5178-5183). If the results of the 150 bp-MSP are used as the standard reference for evaluation of the feasibility of these two quantitative MethyLight assays without setting of cut-off value, the accuracy of the present invention, 115 bp fluorescence MethyLight assay is three times of that of the 70 bp fluorescence MethyLight assay (55.7% vs. 18.6%)

For the classical 70 bp fluorescence MethyLight in this study:
   the sensitivity is 84.1% [37/44];
   the specificity is 34.5% [(58−38)/58];
   the accuracy is 18.6% [84.1%+34.5%−1].
For the novel 115 bp fluorescence MethyLight in this study:
   the sensitivity is 59.1% [26/44];
   the specificity is 96.6% [(58−2)/58];
   the accuracy is 55.7% [59.1%+96.6%−1].

Figure 2:
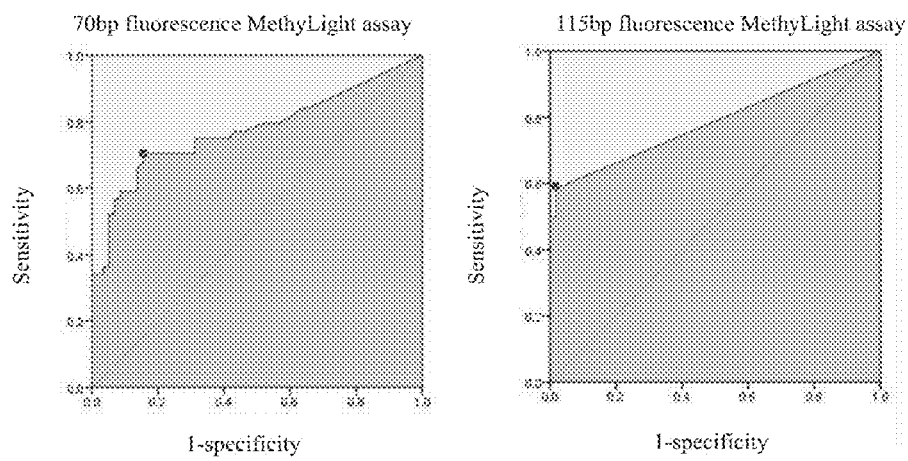
FIG. 2 represents the receiver-operating characteristic curves (ROC curve) of results of p16 methylation in 102 human epithelial dysplasia samples detected by the 70 bp- and 115 bp-MethyLight fluorescence assays.

Plotting the ROC curve by calculating the accuracy using the different relative copy number of p16M as the positive acceptance and rejection criteria (FIG. 2). Use these relative copy number values at which the accuracy is the highest as the cut-off value, and re-calculate the results of p16M-positive rate in these samples, it is found that the accuracy of the method of the present invention, the 115 bp fluorescence MethyLight, is similar to the classical 70 bp fluorescence MethyLight. However, the specificity of the novel 115 bp-MethyLight is significantly higher than that of classical 70 bp MethyLight.

For the classical 70 bp MethyLight when the cut-off value of the relative copy number is set to 0.073:
   the sensitivity is 70.5% [31/44];
   the specificity is 82.8% [(58−10)158];
   the accuracy is 53.3% [82.8%+70.5%−1].
For the novel 115 bp fluorescence MethyLight when the cut-off value of the relative copy number is set to 0.0002:
   the sensitivity is 59.1% [26/44];
   the specificity is 98.3% [(58−1)/58];
   the accuracy is 57.4% [59.1%+98.3%−1].

Among the 102 tested samples, 34 biopsy samples with pathological diagnosis of mild or moderate oral epithelial dysplasia lesions are from patients who are over the age of 60 years and followup for a long-term (Cao et al. Clin Cancer Res 2009, 15:5178-5183). The relationship between p16M by two MethyLight assays and malignant transformation of these oral epithelial dysplasia lesions is further analyzed. Results show that the risk of malignant transformation of the dysplasia lesions containing p16M in the 115 bp novel assay is significantly higher that of the lesions not containing p16M (6/8 vs. 6/22), and said difference has the statistical significance (P=0.036, two-sided). However, the risk of malignant transformation of the dysplasia lesions containing p16M in the 70 bp MethyLight assay is also higher that of the lesions not containing p16M (6/10 vs. 7/24), and the statistical significance can't be observed (P=0.13, two-sided). These results indicate that, comparing with the 70 bp MethyLight assay, the results of the 115 bp novel MethyLight assay in the present invention is more consistent with the results of MSP for detection of p16M, and its clinical significance is also more consistent.

It needs to be noted that the results of using the probe of SEQ ID NO.3 is the same as to that of using the probe of SEQ ID NO.4.

Primer set of the present invention fully meet the requirements of the development of diagnostic kits.

The invention claimed is:

1. A probe and a primer set in the methylation-specific fluorescence assay used to detect methylation of CpG islands in the p16 gene, comprising a pair of oligonucleotide primers and one fluorescence-labeled probe, wherein said pair of oligonucleotide primers comprise the base sequence as shown in SEQ ID NO.1 and SEQ ID NO.2, and said fluorescence-labeled probe comprises the base sequence as shown in SEQ ID NO. 3 or SEQ ID NO.4.

2. A probe and primer set according to claim 1, wherein said primer set is designed based on the nucleotide sequences of the sense-strand or its complementary antisense-strand of the methylated CpG islands of p16 gene after sodium bisulfite modification.

3. A probe and primer set according to claim 2, wherein said nucleotide sequence of the sense-strand comprises the base sequence as shown in SEQ ID NO.8.

* * * * *